United States Patent
Gauthier et al.

(10) Patent No.: US 9,256,947 B2
(45) Date of Patent: Feb. 9, 2016

(54) AUTOMATIC POSITIONING OF IMAGING PLANE IN ULTRASONIC IMAGING

(75) Inventors: Thomas Patrice Jean Arsene Gauthier, Seattle, WA (US); James Robertson Jago, Seattle, WA (US)

(73) Assignee: Koninklijke Philips N.V., Eindhoven (NL)

( * ) Notice: Subject to any disclaimer, the term of this patent is extended or adjusted under 35 U.S.C. 154(b) by 15 days.

(21) Appl. No.: 13/635,460

(22) PCT Filed: Mar. 8, 2011

(86) PCT No.: PCT/IB2011/050964
§ 371 (c)(1),
(2), (4) Date: Dec. 5, 2012

(87) PCT Pub. No.: WO2011/114259
PCT Pub. Date: Sep. 22, 2011

(65) Prior Publication Data
US 2013/0195313 A1  Aug. 1, 2013

Related U.S. Application Data

(60) Provisional application No. 61/315,515, filed on Mar. 19, 2010.

(51) Int. Cl.
| G06T 7/00 | (2006.01) |
| H04N 5/30 | (2006.01) |
| A61B 8/08 | (2006.01) |
| A61B 8/14 | (2006.01) |
| A61B 8/00 | (2006.01) |
| A61B 5/06 | (2006.01) |

(52) U.S. Cl.
CPC ............ *G06T 7/0042* (2013.01); *A61B 8/0833* (2013.01); *A61B 8/0841* (2013.01); *A61B 8/14* (2013.01); *A61B 8/4245* (2013.01); *A61B 8/463* (2013.01); *A61B 8/523* (2013.01); *H04N 5/30* (2013.01); *A61B 5/06* (2013.01)

(58) Field of Classification Search
None
See application file for complete search history.

(56) References Cited

U.S. PATENT DOCUMENTS

| 6,733,458 | B1 | 5/2004 | Steins et al. | |
| 7,270,634 | B2 * | 9/2007 | Scampini et al. | 600/447 |
| 7,604,601 | B2 | 10/2009 | Altmann et al. | |
| 7,860,282 | B2 * | 12/2010 | Boese et al. | 382/128 |
| 8,310,552 | B2 | 11/2012 | Noguchi | |
| 8,449,466 | B2 * | 5/2013 | Duhay et al. | 600/439 |
| 8,663,110 | B2 * | 3/2014 | Kim et al. | 600/437 |
| 2003/0065260 | A1 * | 4/2003 | Cheng et al. | 600/427 |

(Continued)

FOREIGN PATENT DOCUMENTS

| EP | 2147636 A1 | 1/2010 |
| JP | 2005323669 A | 11/2005 |

(Continued)

*Primary Examiner* — Atiba O Fitzpatrick

(57) ABSTRACT

The invention is directed to a method for ultrasonic imaging, in which two-dimensional images (10, 11) are acquired, one of which is aligned with a longitudinal direction of an interventional object (e.g. a needle) (13) to be moved towards a target area (7) within a subject of examination and the other one is intersecting the longitudinal direction of the interventional object (13) and automatically positioned dependent on the automatically determined position and orientation of the interventional object (13). Further, the invention is directed to an ultrasonic imaging device (1) adapted to conduct such a method.

18 Claims, 2 Drawing Sheets

(56) References Cited

U.S. PATENT DOCUMENTS

| | | |
|---|---|---|
| 2004/0106869 A1 | 6/2004 | Tepper |
| 2005/0085730 A1* | 4/2005 | Flesch et al. .................. 600/459 |
| 2007/0055131 A1* | 3/2007 | Deinzer et al. ................ 600/407 |
| 2007/0073155 A1 | 3/2007 | Park et al. |
| 2007/0161905 A1* | 7/2007 | Munrow ....................... 600/459 |
| 2007/0249934 A1* | 10/2007 | Aksit et al. ................... 600/427 |
| 2008/0262348 A1* | 10/2008 | Hashimoto et al. ........... 600/437 |
| 2008/0294052 A1* | 11/2008 | Wilser et al. .................. 600/459 |
| 2009/0018448 A1* | 1/2009 | Seo et al. ...................... 600/443 |
| 2009/0054776 A1* | 2/2009 | Sasaki ........................... 600/443 |
| 2009/0087068 A1* | 4/2009 | Sakaguchi .................... 382/132 |
| 2009/0137907 A1 | 5/2009 | Takimoto et al. |
| 2010/0268067 A1* | 10/2010 | Razzaque et al. ............. 600/424 |
| 2010/0312096 A1* | 12/2010 | Guttman et al. .............. 600/411 |
| 2011/0275908 A1* | 11/2011 | Baumann ...................... 600/301 |
| 2012/0089008 A1* | 4/2012 | Strehl et al. ................... 600/411 |
| 2012/0101370 A1* | 4/2012 | Razzaque et al. ............. 600/424 |

FOREIGN PATENT DOCUMENTS

| | | |
|---|---|---|
| JP | 2007000226 A | 1/2007 |
| JP | 2007190199 A | 8/2007 |
| JP | 2009244853 A | 10/2009 |
| WO | 2007027511 A2 | 3/2007 |
| WO | 2010073165 A1 | 7/2010 |

* cited by examiner

AUTOMATIC POSITIONING OF IMAGING PLANE IN ULTRASONIC IMAGING

FIELD OF THE INVENTION

The invention relates to a method for ultrasonic imaging using at least two two-dimensional images intersecting each other, an ultrasonic imaging device adapted to conduct such a method, a system containing such an ultrasonic imaging device, a computer program for executing such a method and a computer readable medium for storing such a computer program.

BACKGROUND OF THE INVENTION

Real-time ultrasound is routinely used to guide interventional procedures, such as biopsies and local ablative therapies (incl. radio-frequency ablation). With the recent introduction of real-time Multi-Planar Reconstruction (MPR) and bi-plane ultrasound on mechanical and matrix transducers it is now possible to gather in real-time anatomical information in any arbitrary planes. In bi-plane ultrasound imaging, two imaging planes are generated both of which intersect the transducer active aperture. MPR is a method for reconstructing two-dimensional images from a set of raw image data, i.e. from a set of transversal cross-sectional images arbitrary images with different orientation can be calculated, such as frontal, sagittal or oblique cross-sectional images. In MPR, a so determined imaging plane which does not intersect the transducer aperture is called C-plane.

US 2007/0073155 A1 describes a compact ultrasound needle guidance system and method for adjustably target a needle's destination in the imaging plane of a two-dimensional ultrasound image before insertion of a needle into a patient. In this system a needle holder is provided at an ultrasound probe for acquiring a two-dimensional image of a subject of examination. Knowing the position of the needle holder and thus the orientation of the needle, an intersection point of the needle with the two-dimensional image can be determined, assuming that the orientation of the needle is not changed during insertion. This intersection point can be marked when displaying the two-dimensional image on a display. However, this system is not very flexible in use such that there is a need for alternative imaging methods and systems.

SUMMARY OF THE INVENTION

The object of the present invention is to provide an alternative method and system for ultrasonic imaging.

This object is solved with the method and system according to the independent claims. Further advantageous developments are subject of the dependent claims.

According to an embodiment of the invention a method for ultrasonic imaging is provided, in which a first two-dimensional image is acquired which is aligned with a longitudinal direction of an interventional object to be moved, preferably a needle, towards a target area within a subject of examination, such as a patient. This alignment means that the longitudinal axis of the interventional object lies substantially or exactly within the imaging plane of the first image. Further, the position and orientation of the interventional object is automatically determined before or after the first two-dimensional image is acquired. This order depends on which way the position and orientation is determined, preferably this could be done by means of an image feature analysis or by electromagnetic tracking of the interventional object, or by determining the position by optical sensors. In case of using the image feature analysis or the determining by optical sensors, the position of the interventional object can be determined prior to acquiring any image. When using the image feature analysis, at least one image has to be acquired as basis for determining the position of the interventional object. Based on the position and orientation of the interventional object, a positioning of a second two-dimensional image is automatically determined and then the second two-dimensional image is acquired. The second two-dimensional image intersects the longitudinal direction of the interventional object, and preferably the imaging planes of the first and second images are perpendicular to each other. In case, MPR is used, the C-plane is chosen such that it is also normal to the longitudinal axis of the interventional object. The term "acquiring" may include the acquisition of images by means of a transducer and a data processor in case of bi-plane ultrasound, and may include the acquisition of desired images from an available data base in case of MPR. Similarly, the term "acquisition device" may include a transducer as well as a computer or module of a data processor for acquiring desired images from an available data base.

This embodiment enables that the movement of the interventional object to be moved is automatically tracked such that a desired imaging of the subject under examination can be displayed wherein this imaging is fixed to the movement of the interventional object. This way the handling of the imaging system needs less attendance and the user, such as a surgeon, can be more focused on other tasks. Ultrasound presents an advantage over Computed Tomography (CT) in that it provides a true real-time imaging modality for guidance, thereby providing the interventional radiologist with more confidence when guiding the needle to the target area.

According to a further embodiment, a method is provided wherein the step of determining the position and orientation of the interventional object includes the determining of the position of a leading end of the interventional object, in particular a needle tip, and wherein the position of the second image is determined such that the second image is distanced a predetermined distance forward of the leading end.

In this respect, the inventors of this invention realized that, with prior art methods and systems the user does not get a good overview of which obstacles the interventional object may encounter along its trajectory. Thus, a "virtual endoscope" is provided with an ultrasonic imaging device. Preferably, this method involves adjusting a C-plane (when MPR is used) or a transverse plane (when using bi-plane ultrasound) so that it is always slightly forward of the needle tip. When using MPR, the needle shaft is preferably always normal to the C-plane. This imaging plane configuration notably provides the user with information on immediate landscape forward of the needle tip, allowing the user to anticipate and adjust the needle trajectory if needed, in order to avoid for example the hitting of a major vessel.

According to a yet further embodiment, the position and orientation of the interventional object is determining repeatedly, and the positioning of the second image is adapted to a changing position and/or orientation of the interventional object. Thus, the position of the interventional object and performing said adjustment is tracked regularly such that the distance is kept constant while the interventional object is moved. This way, the user gets an update of the landscape information while the interventional object is inserted. The update can be done in real time within defined time intervals.

According to a further embodiment, the method is fully automatic while in another embodiment it interacts with the user for example by requesting to input a desired distance.

According to a yet further embodiment, the method comprises acquiring and displaying more transverse planes positioned at different distances in front of the needle tip. The user can then get an additional overview of what is in the path in front of the needle assuming that he will keep the needle in the current orientation.

Further, the invention provides an ultrasonic imaging device adapted to perform at least one of the above methods, a computer program for executing such a method, and a computer readable medium for storing such a computer program, all of which provide the same advantages as the above mentioned embodiments.

It may be seen as the gist of the invention to provide a method in which ultrasound signals are acquired that enable the display of at least two imaging planes including a region of interest, one of them being aligned with the needle main axis, the other being transverse thereto and positioned at a predetermined distance in front of the needle tip.

These and other aspects of the invention will be apparent from and elucidated with reference to the embodiments described hereafter.

BRIEF DESCRIPTION OF THE DRAWINGS

FIG. 1b is a top view of the imaging planes of FIG. 1a; and

DETAILED DESCRIPTION OF EMBODIMENTS

Figure 1A:
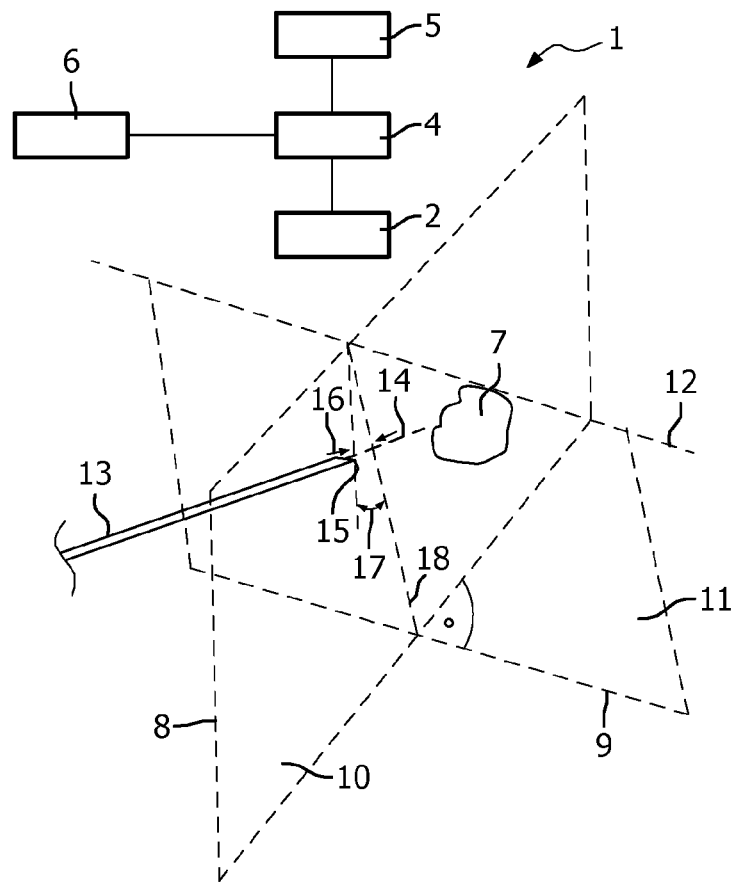
FIG. 1a schematically shows an imaging system with a three-dimensional illustration of two imaging planes.
Figure 1B:
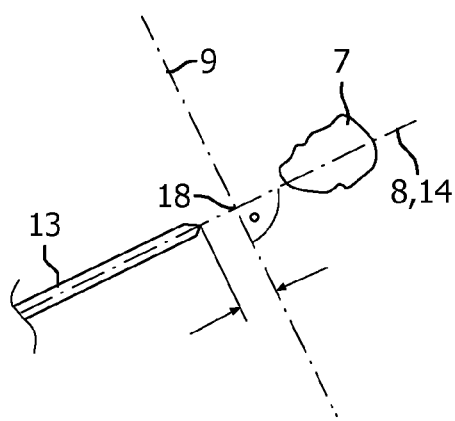

FIG. 1a schematically shows an imaging system 1 according an embodiment of the invention. FIG. 1a further illustrates two imaging planes in a three-dimensional view and FIG. 1b shows a top view projection, as seen from the transducer active aperture, of these imaging planes along a plane containing the longitudinal axis of the needle. FIGS. 1a and 1b exemplary show the case of bi-plane ultrasound imaging, however, the teaching of this invention is equally applicable in Multi-Planar Reconstruction (MPR). In MPR and in bi-plane ultrasound imaging, it is possible to display simultaneously at least two perpendicular imaging planes, one of which lying along the main axis of an interventional device, such as a medical needle, the other of which lying, in the top view of FIG. 1b, perpendicularly to the main axis of the interventional device. Such a configuration is useful when guiding an interventional device to a target lesion under real-time ultrasound guidance.

FIG. 1a shows a transducer 2 for sending and receiving ultrasound signals within a first imaging plane 8, such as an azimuthal plane. Further, the transducer 2 is provided for sending and receiving ultrasound signals within a second imaging plane 9, such as a transversal plane or bi-plane in case of bi-plane ultrasound and a C-plane in case MPR is used. The transducer 2 is preferably a 2D array matrix transducer. Such a 2D array matrix transducer comprises, on a surface facing the subject to be examined, an array of transducer elements arranged for example in a chessboard or segmented ring like fashion. Each of these transducer elements is provided with its own transmit-receive-channel, thus the individual transducer elements can be controlled individually. By driving them accordingly, the resulting ultrasonic beam can be tilted, rotated (about a vertical axis or an axis along the center beam of the transducer) and focused electronically without requiring physically rotating transducers as in prior devices. The transducer 2 is connected with a data processor 4 which is adapted to control the transducer 2. Further, the data processor 4 reconstructs two-dimensional images 10 and 11 within the imaging planes 8 and 9, respectively, corresponding to the ultrasound signals acquired by the transducer 2. The images 10 and 11 provide reconstructions of a subject of examination, such as a patient (not shown). A specific target area 7, such as a target lesion, of the subject is crossed by at least the first imaging plane 8. These images 10 and 11 are displayable by a display 5 which is in connection with the data processor 4. Also, the imaging system 1 comprises a user interface 6 provided for a user to manipulate the imaging system 1.

FIG. 1a further shows a needle 13 which could also be any other interventional device. The first imaging plane 8 is positioned such as to be aligned with a longitudinal axis 14 of the needle 13, i.e. the longitudinal axis lies within the first imaging plane 8. By applying an image feature analysis on at least the first image 10, such as a shape recognition algorithm well known in the art, the position and orientation of the needle 13, in particular a shaft orientation and the position of the needle tip 15, can be automatically recognized in the image 10. For this purpose the data processor 4 can execute the feature analysis method and thus function as a detection device.

In an alternative way, the position and orientation of the needle 13, in particular the shaft orientation and the position of the needle tip 15, is automatically recognized by electromagnetic tracking, such as an electromagnetic needle tip tracking introduced by Traxtal, Inc. realizing an automatic tip tracking capability. For this purpose, a separate electromagnetic tracking device would have to be provided as known from the state of the art, which would be connected with the data processor 4.

This information is then used in real-time to position and/or orient the second imaging plane 9 such that it is slightly forward of the needle tip 15 by a distance 16 which is the distance along the longitudinal axis 14 between the needle tip 15 and the intersection point of the longitudinal axis 14 with the second imaging plane 9. In FIG. 1b a projection of the distance 16 into the top view is shown, wherein also such a projection could be used as relevant distance. This distance 16 can be set by controlling the individual transducer elements of the transducer 2 such that the resulting ultrasonic beam is rotated about a vertical axis or an axis along the center beam of the transducer and tilted about an axis 12 such that a tilting movement is achieved as indicated by an arrow marked with reference numeral 17. Reference numeral 18 indicates an intersection line of the first and second imaging plane. In case of using MPR, the second imaging plane 9 may additionally be chosen to be normal to the longitudinal axis 14. The preferred distance between the needle tip 15 and the second imaging plane 9 should be such that it allows the user enough time to make adjustments to the needle trajectory if necessary. The preferred distance is anywhere between a few millimeters to a few centimeters. The distance is more preferably in the range of 1-5 mm, and is either determined automatically and repeatedly by the imaging system, determined automatically once and kept constant during an imaging procedure, or determined by a user by means of the user interface 6. If the distance is determined automatically, it may be determined depending on the type of the interventional object, the moving speed of the interventional object, the subject of examination and/or a type of the target area. In this context, the embodiment might comprise an innovative interface for the user or operator to specify the distance between the second imaging plane 9 and the needle tip 15. For example, the user may be prompted to enter a desired distance in centimeters or millimeters which, when entered, triggers the imaging system to acquire and display a second imaging plane 9 at the desired distance forward of the needle tip 15.

Having the position and/or orientation of the needle 13, the intersection point of the longitudinal axis 16 with the second imaging plane 9 can be marked in the acquired second image 11 when displayed on the display 5, accordingly. In use, the imaging planes 8 and 9 will follow the movement of the needle in order to achieve a live ultrasound image or images. A marker is superimposed on the live ultrasound image for example by crosshairs or by circling the intersection point. Thus, the expected path of the needle can be displayed.

In this embodiment, information on the needle tip 15 and the shaft orientation drives the transducer 2 (ultrasound scanner or beamformer) in real-time and determines how the second imaging plane 9 (transverse plane) is being created. When the ultrasound imaging system 1 is operating in the MPR mode (which is capable of a four-dimensional or C-plane mode), the transducer need not be positioned/oriented since all of the imaging planes are being collected. In this case, the adjustments are applied to the MPR image reconstruction step, which may be either on the ultrasound system imaging system or on an external computing device.

A refinement to the above might be to allow the user or operator to quickly slide the second imaging plane 9 along the needle shaft to either bring it back to the needle tip 15 or to lead it away from the needle tip 15 to be able to anticipate what the needle trajectory is going to be with respect to the subject of examination, such as a surrounding anatomy.

Figure 2:
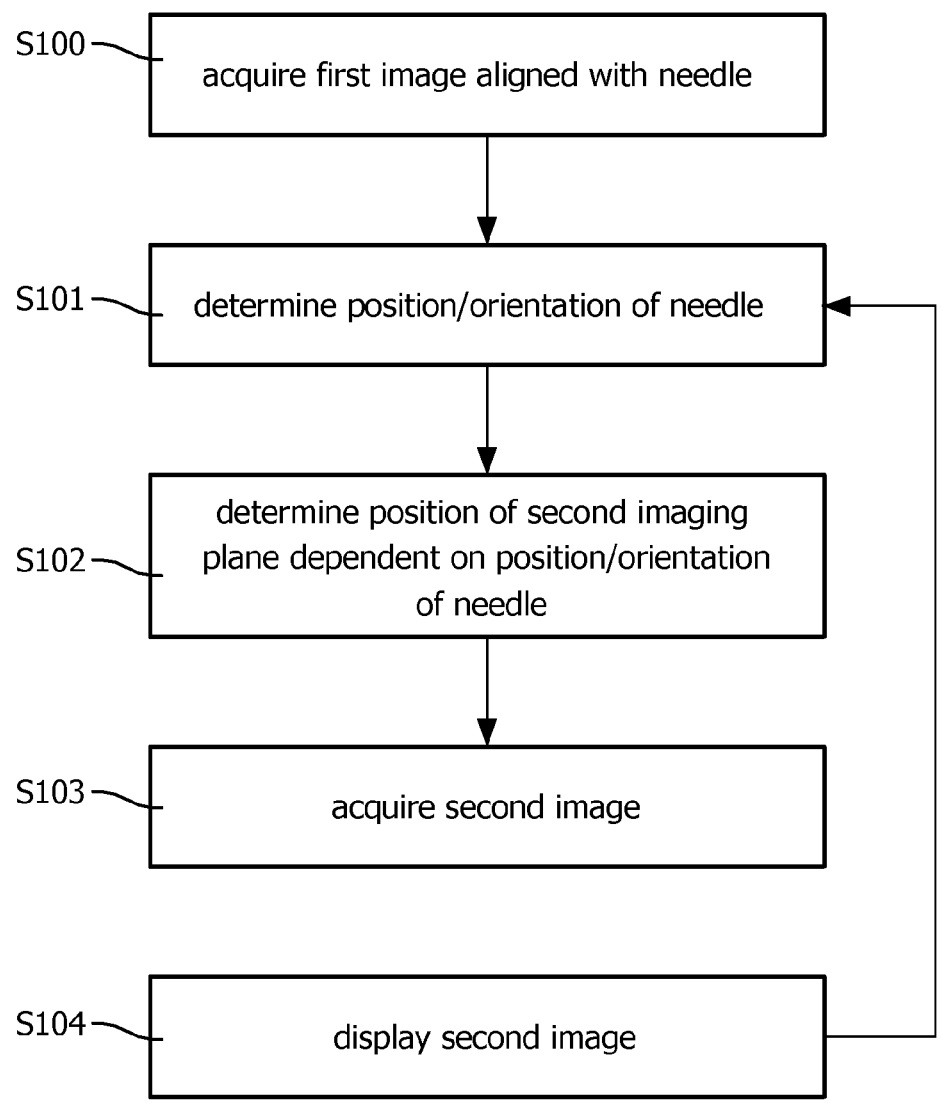
FIG. 2 is a flowchart illustrating the method for ultrasonic imaging according to an embodiment of the invention.

FIG. 2 is a flowchart illustrating the above described method for automatic positioning of the second imaging plane 9 with reference to the shown method steps. In this Figure, the case is illustrated in which the position and orientation of the needle 13 is determined by means of an image feature analysis when conducting bi-plane imaging. In a first step S100, a user aligns the first imaging plane 8 along the shaft of the needle 13. For this purpose, the first image 10 is displayed on the display 5. This first imaging plane 8 also shows the needle tip 15, such that in the next step S101 due to the application of an image feature analysis the position and orientation of the needle 13 is determined. More exact position and orientation data may be achieved when initially an additional image which is perpendicular to the first image 8 (and perpendicular to the needle shaft in a top view as seen from the transducer active aperture), is positioned at the needle tip 15 by the user. Alternatively, to the alignment of the first imaging plane 8 by the user, this alignment could be realized automatically by acquiring an image, analyzing the image by a feature analysis method with respect to presence, position and orientation of the needle, updating the position of the first imaging plane 8 and repeating this until the needle 13 is exactly aligned with the longitudinal axis 14.

Based on the determined position and orientation of the needle 13, and in particular based on the shaft orientation and the position of the needle tip 15, in step S102, the position of the second imaging plane 9 is determined automatically. Based on this information, the second transducer 3 can be positioned (e.g. tilted) as mentioned above. In step S103, an image within the second imaging plane 9 can be acquired, which shows the expected path of the needle 13, i.e. the image which is a predetermined distance forward of the needle tip 15. In step S104, this second image 9 is then displayed on the display 5, wherein the intersection of the second image with the longitudinal direction of the interventional object is marked. At least steps S101 to S104 are repeatedly executed in order to trace a movement of the needle 13 and to adapt the positioning of the second imaging plane 9 accordingly. Also the first step S100 can be included into the repeated loop every time, every few times or when changing the orientation of the needle, in order to ensure that the first image 10 is kept aligned with the first imaging plane 10.

When using electromagnetic tracking of the needle 13, the execution order of the steps S100 and S101 is interchanged. In this case, the position and orientation of the needle 13 is determined first. Based on this information the first and second image 10 and 11 may be acquired substantially simultaneously wherein the first image is aligned with the needle 13 and the second image 11 is distanced a predetermined distance in front of the needle tip 15.

According to a modification of this embodiment, and preferably in connection with MPR imaging, multiple C-planes are displayed simultaneously to provide the user with more information on what the needle will encounter should its trajectory remain the same. For example, each C-plane may be normal to the needle shaft and located at a given distance forward of the needle tip 15, e.g. a first C-plane located 2 mm forward of the needle tip 15, a second C-plane located 5 mm forward of the needle tip 15 and a third C-plane located 20 mm, etc. The additional information provided to the user on structures of the subject under examination present forward of the needle tip 15 may be of additional help in correcting early the needle trajectory, e.g. to avoid hitting a major vessel. This may also be achieved with bi-plane ultrasound imaging, wherein in this case multiple transversal planes would be provided instead of C-planes.

These multiple images in front of the needle tip 15 can be displayed on the display 5 wherein markers, such as crosshairs or a circle, show the intersection of the longitudinal axis of the needle 15 with the individual view intersecting the longitudinal axis of the needle 15, respectively. In this connection, the longitudinal axis of the needle or a projected needle tip trajectory may be displayed on the multiple C-planes as a red dot or a red circle which gets smaller as the needle tip 15 actually approaches a given C-plane.

These multiple images in front of the needle tip 15 could be merged to a video sequence. This way the surgeon could interrupt the interventional procedure and play the video sequence of the images in front of the needle tip 15. This way, the operator may have the ability to record a sequence of C-planes located forward of the needle tip 15 and then play the sequence back to plan the needle trajectory. In other words, the size and or illustration of the marker could be dependent on the distance 16. Thus, if the acquisition of the C-planes is repeated every few seconds (e.g. 3 seconds) when moving the needle, the marker circle becomes smaller continuously and is enlarged abrupt when the acquisition is repeated.

Advantageously there can be provided an innovative user interface 6 by means of which the user may enter on the display 5 the distance 16 between the second imaging plane 9 and the needle tip 15, the number of transverse planes/C-planes (total number of second plane+further planes intersecting the longitudinal direction of the needle 13) displayed on the display 5 and the position of the transverse planes/C-planes with respect to the needle tip 15.

The above embodiment was explained by referring to 2D array matrix transducer. However, the present invention could also be implemented by using a mechanical transducer in which the array of piezoelectric elements is mechanically scanned back and forth over a volume of interest. Also, a separate transducer for each imaging plane might be possible.

It is explicitly intended that the teaching of this invention covers any combination of the above described embodiments or modifications.

While the invention has been illustrated and described in detail in the drawings and foregoing description, such illustration and description are to be considered illustrative or exemplary and not restrictive and it is not intended to limit the invention to the disclosed embodiments. The mere fact that certain measures are recited in mutually different dependent claims does not indicate that a combination of these measures cannot be used advantageously. Any reference signs in the claims should not be construed as limiting the scope of the invention.

The invention claimed is:

1. A method for ultrasonic imaging, comprising the steps of:
   acquiring a first ultrasound image corresponding to a first image plane which is aligned with a longitudinal direction of an interventional object to be moved towards a target area within a subject of examination;
   positioning a second image plane automatically based on an automatically determined position and orientation of the interventional object, wherein the second image plane is positioned to intersect the longitudinal direction of the interventional object; and
   acquiring a second ultrasound image corresponding to the second image plane.

2. The method according to claim 1, wherein the step of determining the position and orientation of the interventional object includes the determining of the position of a leading end of the interventional object, and wherein the position of the second image is determined such that the second image is distanced a predetermined distance forward of the leading end.

3. The method according to claim 1, wherein the position and orientation of the interventional object is determining repeatedly, and the positioning of the second image is adapted to a changing position and/or orientation of the interventional object.

4. The method according to claim 1,
   acquiring at least one further ultrasound image intersecting the longitudinal direction of the interventional object;
   wherein the at least one further ultrasound image is positioned such that it is distanced a predetermined interval from the second image.

5. The method according to claim 1, wherein the position and orientation of the interventional object is determined by an image feature analysis.

6. The method according to claim 1, wherein the position and orientation of the interventional object is determined by electromagnetic tracking of the interventional object.

7. The method according to claim 2, wherein the distance is adjustable by a user.

8. The method according to claim 2, wherein the distance is automatically determined depending on the type of the interventional object, the moving speed of the interventional object, the subject of examination and/or a type of the target area.

9. The method according to claim 1, wherein
   the first ultrasound image is displayed on a display screen; and
   the second ultrasound image is displayed on the display screen.

10. The method according to claim 9, wherein an intersection of the second image with the longitudinal direction of the interventional object is marked in the displayed first ultrasound image.

11. An ultrasonic imaging device comprising:
    an acquisition device comprising a transducer for acquiring a first and second ultrasound image corresponding to a first and second image plane, respectively;
    a data processor configured to determine a position and orientation of an interventional object to be moved to a target area within a subject of examination;
    wherein the ultrasonic imaging device is configured, during an interventional procedure, to align the first image plane with a longitudinal direction of the interventional object, wherein the second image plane intersects the longitudinal direction of the interventional object, and
    wherein the acquisition device is adapted to acquire the second ultrasound image at a position based on the position and orientation of the interventional object during the interventional procedure.

12. The ultrasonic imaging device according to claim 11, wherein the detection device is adapted to determine the position of the leading end of the interventional object, and wherein the acquisition device is adapted to acquire the second image such that the second image is distanced a predetermined distance forward of the leading end.

13. A non-transitory computer readable medium for storing a program, which, when executed by at least one processor, causes the at least one processor to perform the method for ultrasonic imaging according to claim 1.

14. The method of claim 1, wherein ultrasound signals from the first and second image planes are acquired using a two-dimensional array transducer.

15. The method of claim 1, further comprising displaying at least one of a first and second ultrasound image generated from the ultrasound signals acquired from the first and second image planes, respectively.

16. The imaging device of claim 11, wherein the transducer comprises a two-dimensional array transducer.

17. The imaging device of claim 11, further comprising a display configured to display at least one of the first and second ultrasound images.

18. The imaging device of claim 11, wherein the data processor is configured to determine the position and orientation of the interventional object based on image feature analysis or electromagnetic tracking of the interventional object.

* * * * *